(12) United States Patent
Qiao et al.

(10) Patent No.: US 6,815,078 B2
(45) Date of Patent: Nov. 9, 2004

(54) SUBSTRATE FOR PROTEIN MICROARRAY CONTAINING FUNCTIONALIZED POLYMER

(75) Inventors: Tiecheng A. Qiao, Webster, NY (US); Jeffrey W. Leon, Rochester, NY (US); Thomas L. Penner, Fairport, NY (US); Zhihao Yang, Webster, NY (US)

(73) Assignee: Eastman Kodak Company, Rochester, NY (US)

(*) Notice: Subject to any disclaimer, the term of this patent is extended or adjusted under 35 U.S.C. 154(b) by 300 days.

(21) Appl. No.: 10/091,644

(22) Filed: Mar. 6, 2002

(65) Prior Publication Data

US 2003/0170474 A1 Sep. 11, 2003

(51) Int. Cl.[7] .......................... B32B 9/04; C12N 11/06; G01N 33/53; G01N 33/544; G01N 33/549
(52) U.S. Cl. ................... 428/478.2; 435/181; 435/960; 436/528; 436/532; 436/809
(58) Field of Search ....................... 428/478.2; 435/181, 435/960; 436/528, 532, 809

(56) References Cited

U.S. PATENT DOCUMENTS

| | | |
|---|---|---|
| 4,161,407 A | 7/1979 | Campbell |
| 4,355,108 A * | 10/1982 | Gaddy et al. ............... 435/165 |
| 4,548,869 A | 10/1985 | Ogawa et al. |
| 5,110,833 A | 5/1992 | Mosbach |
| 5,981,734 A | 11/1999 | Mirzabekov et al. |

FOREIGN PATENT DOCUMENTS

| | | |
|---|---|---|
| EP | 1 106 603 A2 | 6/2001 |
| WO | WO 95/04594 | 2/1995 |
| WO | WO 98/29736 | 7/1998 |
| WO | WO 00/04382 | 1/2000 |
| WO | WO 00/04389 | 1/2000 |
| WO | WO 01/40312 | 6/2001 |
| WO | WO 01/40803 | 6/2001 |

OTHER PUBLICATIONS

*Analytical Biochemistry* 278, 123–131 (2000), "Protein Microchips: Use for Immunoassay and Enzymatic Reactions," by Pavel Arenkov et al.

Edgar B. Gutoff, Chapter 1 of "Modern Coating and Drying Technology," (Interfacial Engineering Series; v.1), 1992, VCH Publishers Inc. New York, N.Y.

*Science*, vol. 249, 505–510, 1990, "Systematic Evolution of Ligands by Exponential Enrichment: RNA Ligands to Bacteriophage T4 DNA Polymerase," Craig Tuerk and Larry Gold.

*Nature*, vol. 346, pp 818–822, 1990, "In vitro selection of RNA molecules that bind specific ligands," Andrew D. Ellington & Jack W. Szostak.

Qiao et al., Method for Making Biochip Substrate, USSN 10/020,747 (Attorney Docket No. 82429/D–W), filed Nov. 30, 2001.

P.I. Rose, "The Theory of the Photographic Process," 4th edition, T.H. James Ed., pp. 51–67, 1977.

* cited by examiner

Primary Examiner—Nathan M. Nutter
(74) Attorney, Agent, or Firm—Kathleen Neuner Manne

(57) ABSTRACT

A gelatin-based substrate for fabricating protein arrays, the substrate comprising:
  gelatin having at least one surface;
  a polymer scaffold affixed to the gelatin surface;
wherein the polymer in the scaffold is rich in reactive units capable of immobilizing proteins.

27 Claims, No Drawings

SUBSTRATE FOR PROTEIN MICROARRAY CONTAINING FUNCTIONALIZED POLYMER

FIELD OF THE INVENTION

The present invention relates to fabricating protein microarrays in general and in particular to a method that utilizes a gelatin-based substrate wherein the gelatin surface is modified to improve specific attachment of biological molecules.

BACKGROUND OF THE INVENTION

The completion of Human Genome project spurred the rapid growth of a new interdisciplinary field of proteomics which includes: identification and characterization of complete sets of proteins encoded by the genome, the synthesis of proteins, post-translational modifications, as well as detailed mapping of protein interaction at the cellular regulation level.

While 2-dimensional gel electrophoresis in combination with mass spectrometry still remains the dominant technology in proteomics study, the successful implantation and application of DNA microarray technology to gene profiling and gene discovery have prompted scientists to develop protein microarray technology and apply microchip based protein assays to the field of proteomics. For example, in WO 00/04382 and WO 00/04389, a method of fabricating protein microarrays is disclosed. A key element in the disclosure is a substrate consisting of a solid support coated with a monolayer of thin organic film on which protein or a protein capture agent can be immobilized.

Nitrocellulose membrane was widely used as a protein blotting substrate in Western blotting and enzyme linked immunosorbent assay (ELISA). In WO 01/40312 and WO 01/40803, antibodies are spotted onto a nitrocellulose membrane using a gridding robot device. Such spotted antibody microarrays on a nitrocellulose membrane substrate have been shown to be useful in analyzing protein mixture in a large parallel manner.

In WO 98/29736, L. G. Mendoza et al. describe an antibody microarray with antibody immobilized onto a N-hydroxysuccinimidyl ester modified glass substrate. In U.S. Pat. No. 5,981,734 and WO 95/04594, a polyacrylamide based hydrogel substrate technology is described for the fabrication of DNA microarrays. More recently, in *Anal. Biochem.* (2000) 278, 123–131, the same hydrogel technology was further demonstrated as useful as a substrate for the immobilization of proteins in making protein microarrays.

In the above cited examples, the common feature among these different approaches is the requirement of a solid support that allows covalent or non-covalent attachment of a protein or a protein capture agent on the surface of said support. In DNA microarray technology, a variety of surfaces have been prepared for the deposition of pre-synthesized oligos and PCR prepared cDNA probes. For example, in EP 1 106 603 A2 a method of preparing vinylsulfonyl reactive groups on the surface to manufacture DNA chip is disclosed. Even though the invention is useful in preparing DNA chip, it is not suitable for protein microarray applications. Unlike DNA, proteins tend to bind to surfaces in a non-specific manner and, in doing so, lose their biological activity. Thus, the attributes for a protein microarray substrate are different from those for a DNA microarray substrate in that the protein microarray substrate must not only provide surface functionality that are capable of interacting with protein capture agents, but must also resist non-specific protein binding to areas where no protein capture agents have been deposited.

Bovine serum albumin (BSA) has been demonstrated to be a useful reagent in blocking proteins from non-specific surface binding. Polyethylene glycol and phospholipids have also been used to passivate surfaces and provide a surface resistant to non-specific binding. However, all of these methods suffer disadvantages either because surface preparation takes a long time or because the method of surface modification is complex and difficult, making the method less than an ideal choice for large scale industrial manufacture.

U.S. Ser. No. 10/020,747, describes a low cost method of making protein microarray substrate using gelatin coating to create a reactive surface for immobilization of protein capture agents. While the gelatin modified surface effectively eliminates non-specific protein binding, the number of reactive sites on the surface are limited by the intrinsic functional groups in gelatin and the type of chemical agents (A-L-B) employed. Since the number of reactive sites on the surface directly determine the ultimate signal detection limit, it is desirable to create a surface with higher number of reactive sites that serve as a matrix on a solid support for the attachment of protein capture agents. The art needs a substrate with chemical functionality for the immobilization of protein capture agents, but such substrate must not bind proteins to areas on the gelatin surface that are without immobilized protein capture agents.

SUMMARY OF THE INVENTION

The present invention seeks to solve some of the problems discussed above by providing:
A gelatin-based substrate for fabricating protein arrays, the substrate comprising:
  gelatin having at least one surface;
  a polymer scaffold affixed to the gelatin surface; and
  the polymer scaffold in interaction with/bonded to/a tri-functional compound A-L-B;
wherein A is a functional group capable of interacting with the protein scaffold; L is a linking group capable of interacting with A and with B; and B is a functional group capable of interacting with a protein capture agent.

Also A method of making a gelatin-based substrate for fabricating protein arrays comprising the steps of:
  providing a support;
  coating on the support a composition containing gelatin;
  bonding a polymer scaffold to a surface of the gelatin;
    wherein the polymer in the scaffold is rich in reactive units capable of immobilizing proteins.

The invention is particularly useful in fabricating protein microarrays. It provides a substrate with functionalities capable of interacting specifically with protein capture agents immobilized on its surface and that is substantially resistant to non-specific binding.

Substrates prepared with gelatin modified according to this invention require a very low concentration of biological sample in fabricating protein microarrays when compared with unmodified gelatin substrates. The gelatin substrates of the invention can be readily manufactured at low cost. The usefulness of the claimed substrate for protein attachment is demonstrated below in the examples, using several chemical modification methods and enzyme linked immunosorbent assay (ELISA).

DETAILED DESCRIPTION OF THE INVENTION

In general, a protein microarray can be prepared by first modifying a solid substrate, namely the protein microarray substrate, followed by depositing various protein capture agents onto the modified substrate at pre-defined locations. As used herein, the term "substrate" refers to the gelling agent (e.g., gelatin) that forms the surface to which a polymer scaffold may be grafted. The substrate is coated on a base called the "support" herein. Supports of choice for protein microarray applications can be organic, inorganic or biological. Some commonly used support materials include glass, plastics, metals, semiconductors. The support can be transparent or opaque, flexible or rigid. In some cases, the support can be a porous membrane e.g. nitrocellulose and polyvinylidene difluoride, and the protein capture agents are deposited onto the membrane by physical adsorption. However, to improve robustness and reproducibility, it is more desirable to immobilize the protein capture agents onto a substrate through chemical covalent bonding.

To immobilize protein capture agents onto a solid substrate, the substrate needs to be modified by certain chemical functional agents. Preferably, the chemically functional agent is a bi-functional molecule which can be represented as A-L-B, in which A and B are chemical functionalities that are capable of reacting or interacting with gelatin and protein capture agent molecules to be immobilized on the substrate and L is linkage group. Preferably, L is a diradical of such a length that the shortest through-bond path between the ends that connect A to B is not greater than 10 atoms.

There are two classes of bi-functional agents: 1). homofunctional agent if A=B; and 2). heterofunctional agent if A≠B. Some commonly used A and B include but are not limited to, aldehyde, epoxy, hydrazide, vinyl sulfone, succinimidyl ester, carbodiimide, maleimide, dithio, iodoacetyl, isocyanate, isothiocyanate, aziridine. The linking group L comprises any reasonable combination of relatively non-labile covalently bonded chemical units sufficient to connect the two functionalities A and B. These chemical units can consists of, but are not necessarily limited to, a single bond, a carbon atom, an oxygen atom, a sulfur atom, a carbonyl group

a carboxylic ester group

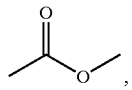

a carboxylic amide group

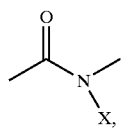

a sulfonyl group

a sulfonamide group

an ethyleneoxy group, a polyethyleneoxy group, or an amino group

where substituents X, Y, and Z are each independently a hydrogen atom, or an alkyl group of 1–10 carbon atoms; and linear or branched, saturated or unsaturated alkyl group of 1 to 10 carbon atoms (such as methyl, ethyl, n-propyl, isopropyl, t-butyl, hexyl, decyl, benzyl, methoxymethyl, hydroxyethyl, iso-butyl, and n-butyl); a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanophenyl); and a substituted or unsubstituted cycloalkyl group of 5 to 14 carbon atoms such as cyclopentyl, cyclohexyl, and cyclooctyl); a substituted or unsubstituted, saturated or unsaturated heterocyclic group (such as pyridyl, primidyl, morpholino, and furanyl); a cyano group. Some solubilizing groups can also be introduced into A-L-B and examples of these solubilizing groups include, but are not limited to, carboxylic acid, sulfonic acid, phosphonic acid, hydroxamic acid, sulfonamide, and hydroxy groups (and their corresponding salts). A and B can also be in the form of readily reactive functionalities towards crosslinkers, examples include but not limited to carboxy, amino, and chloromethyl, etc. A and B can be affinity tags that are capable of interacting non-covalently with the protein capture agents intended to be immobilized onto the substrate. For example, some commonly used tag systems include, but are not limited to, streptavidin and biotin, histidine tags and nickel metal ions, glutathione-S-transferase and glutathione. One skilled in the art should be able to create a fusion protein capture agent using recombination DNA technology and an element of tag recognition unit can be introduced into protein capture agent in this way.

The present invention is designed to attain very high densities of chemical moieties that are useful in the immobilization of proteins. To accomplish this, the invention employs a "polymer scaffold" strategy. For the purposes of this invention, the term "polymer scaffold" refers to a linear or branched polymer, rich in specific functionalities, that extends out in a 3-dimensional fashion from a surface. In this case, functional groups consist of chemical units capable of immobilizing proteins and the surface is protein. In one basic strategy for the preparation of a protein-receptive polymer scaffold, a precursor polymer is utilized which is rich in units that are capable of being converted into chemical functions that will immobilize proteins. The precursor polymer is affixed to a gelatin surface and then converted to a protein-receptive form by post-treatment with a chemical agent. By "affixed" it is meant that the precursor polymer is applied to the gelatin surface and adheres to the gelatin by any of a number of chemical and physical attractive mechanisms including ionic interactions, covalent bonds, coordinative bonds, hydrogen bonds, and Van-der-Waals interactions.

In a preferred embodiment, the chemical agent will be one of the A-L-B structures defined above and the precursor polymer will be rich in such reactive units as thiols, amines, phosphines, alcohols, or carboxylic acids. Preferably the reactive unit is a primary or secondary amine. Specific polymers which can be used for this purpose may be selected from the set consisting of, but not necessarily limited to poly (propyleneimine) and polymers and copolymers of N-aminopropyl (meth)acrylamide and secondary amine derivatives thereof, N-aminoethyl (meth)acrylate and secondary amine forms thereof, diallyamine, vinylbenzylamine, vinylamine, (meth)acrylic acid, vinylbenzyl mercaptan, and hydroxyethyl(meth)acrylate. Preferably, the polymer is poly(vinylamine), poly (propyleneimine), or poly(N-aminopropyl methacrylamide).

The affixing of the scaffold polymer to the surface of the gelatin can be achieved using any chemical agent or technique that is known to result in the formation of a covalent bond between the reactive units of the polymer and either the amine or carboxylic acid functionality of the gelatin. For example, a dehydrating agent such as a carbodiimide, a pyridyl dication ether, or a carbamoylpyridinium compound can be used to bind an amine-containing polymer or a carboxylic acid-containing polymer to a gelatin surface via amide bonds. Similarly, a bis(vinylsulfonyl) compound can be used to bind poly(ethyleneimine) to a gelatin surface. Once the scaffold polymer is affixed to the gelatin surface, it is then treated with an excess of the appropriate A-L-B compound to afford the reactive surface with a high level of reactive units.

A second basic strategy for the preparation of a protein-receptive polymer scaffold involves the direct affixing onto the gelatin surface of a polymer rich in chemical functions that will immobilize proteins. Such functions include, but are not necessarily limited to include but are not limited to: aldehyde, epoxy, hydrazide, vinyl sulfone, succinimidyl ester, carbodiimide, maleimide, dithio, iodoacetyl, isocyanate, isothiocyanate, and aziridine. Additionally, more than one type of polymer scaffold polymer may be affixed to the same gelatin substrate.

Formula I represents a preferred polymer for forming the polymer scaffold:

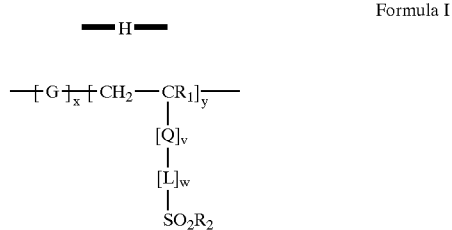

Formula I wherein
$R_1$ is a hydrogen atom or a $C_1$–$C_6$ alkyl group. Preferably $R_1$ is a hydrogen atom.
Q is —$CO_2$—, or $CONR_1$—;
v is 1 or 0;
w is 1–3;
L is a divalent linking group containing at least one linkage selected from the group consisting of —$CO_2$— and —$CONR_1$, and containing 3–15 carbon atoms, or a divalent atom containing at least one linkage selected from the group consisting of —O—, —$N(R_1)$—, —CO—, —SO—, —$SO_2$—, —$SO_3$—, —$SO_2N(R_1)$—, —$N(R_1)CON(R_1)$— and —$N(R_1)CO_2$—, and containing 1–12 carbon atoms in which $R_1$ has the same meaning as defined above;
$R_2$ is —CH=CH2 or —CH2—CH2$X_1$ wherein $X_1$ is a substituent replaceable by a nucleophilic group or releasable in the form of $HX_1$ by a base. $X_1$ may be, but is not necessarily limited to —$S_2O_3^-$, —$SO_4^-$, —Cl, —Br, —I, quaternary ammonium, pyridinium, and —CN, and sulfonate esters (such as mesylate and tosylate); x and y both represent molar percentages ranging from 10 to 90 and 90 to 10.

Preferably, x and y range from 25 to 75 and 75 to 25, respectively.

In a preferred embodiment of this invention, a polymer containing pendant vinylsulfone or vinylsulfone precursor units may be reacted with the gelatin in order to provide a polymer scaffold. Polymers preferred for this embodiment are represented by the structure in Formula I, and consist of the polymerization products of a "G" monomer, which affords to polymer with favorable solubility properties, and a "H" monomer, which contains the vinylsulfone moiety or, more preferably, a vinylsulfone precursor function, such as a sulfonylethyl group with a leaving group in the β-position. More than one type each of G and H monomers may be present in the same polymer. Although the polymer may have any molecular weight, molecular weights (Mn) between 1000 and 200,000 AMU are preferred. Molecular weights between 2000 and 50,000 AMU are especially preferred provided that the polymer is soluble in water or a mixture of water and water-miscible solvents (such as methanol, ethanol, acetone, tetrahydrofuran, etc.). Additional monomers can be incorporated in order to modify properties such as glass transition temperature, surface properties, and compatibility with other formulation components as needed for specific applications. Selection of additional monomers will be application dependent and will be obvious to one skilled in the art.

G is a polymerized α,β-ethylenically unsaturated addition polymerizeable monomer which imparts water-solubility to the polymer. The monomer from which G can be derived include both ionic and nonionic monomers. Ionic monomers may include, for example, anionic ethylenically unsaturated monomers such as 2-phosphatoethyl acrylate potassium salt, 3-phosphatopropyl methacrylate ammonium salt, acrylamide, methacrylamides, maleic acid and salts thereof, sulfopropyl acrylate and methacrylate, acrylic and methacrylic acids and salts thereof, N-vinylpyrrolidone, acrylic and methacrylic esters of alkylphosphonates, styrenics, acrylic and methacrylic monomers containing amine ammonium functionalities, styrenesulfonic acid and salts thereof, acrylic and methacrylic esters of alkylsulfonates, vinylsulfonic acid and salts thereof. Nonionic monomers may include monomers containing hydrophilic, nonionic units such as poly(ethylene oxide) segments, carbohydrates, amines, amides, alcohols, polyols, nitrogen-containing heterocycles, and oligopeptides. Examples include, but are not limited to poly(ethylene oxide) acrylate and methacrylate esters, vinylpyridines, hydroxyethyl acrylate, glycerol acrylate and methacrylate esters, (meth)acrylamide, and N-vinylpyrrolidone.

Preferably, G is the polymerized form of acrylamide, sodium 2-acrylamido-2-methanepropionate, sulfopropyl acrylate and methacrylate salts, or sodium styrenesulfonate.

Monomer H is the polymerized form of a vinylsulfone or vinylsulfone precursor unit covalently bound to a polymerizeable α, β-ethylenically unsaturated function by an organic spacer which consists of Q and L, of which Q is an optional component.

Vinylsulfone and vinylsulfone-containing precursor "H" monomers useful in this embodiment include, but are not necessarily limited to those compounds disclosed in U.S. Pat. Nos. 4,548,869 and 4,161,407 (incorporated herein by reference) as well as those compounds in Formula II.

Although the polymer may have any molecular weight, molecular weights (Mn) between 1000 and 200,000 AMU are preferred. Molecular weights between 2000 and 50,000 AMU are especially preferred.

Gelatin has been used in the photographic industry as a binder for various chemical components, and the process of making high quality gelatin is well established in industry. Because gelatin is made of biological materials, it is biologically compatible with protein capture agents on the protein microarray. The gelatin coated surface provides a biologically benign surface for the immobilization of protein capture agents onto the protein microarray. As shown in this invention, gelatin also renders a surface that substantially reduces background noise that is a result of non-specific binding. Normally, gelatin is coated onto a support and gelation occurs through a process by which gelatin solutions or suspensions of gelatin and other materials form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation which is of the latter type. The process of gelation or setting is characterized by a discontinuous rise in viscosity. (See, P. I. Rose, "The Theory of the Photographic Process", $4^{th}$ Edition, T. H. James ed. pages 51 to 67).

The gelatin substrate described in this invention can either be coated as is on any solid support, or with one or a combination of multiple hardening agents mixed in the gel. The level of the hardening agent should be from 0 to 20 wt. %, and preferably 0.5 to 8 wt. %, of the total gelatin coated.

There are two types of gelatin: acid pretreated and alkaline pretreated. The preferred gelatin is alkaline pretreated gelatin from bovine bone marrow, but gelatin can also come from other sources. Examples include, but are not limited to, pig gelatin, fish gelatin. The bi-functional agent A-L-B can be introduced either during or after the gelatin coating onto a solid support.

Coating methods are broadly described by Edward Cohen and Edgar B. Gutoff in Chapter 1 of "Modem Coating And Drying Technology", (Interfacial Engineering Series; v.1), (1992), VCH Publishers Inc., New York, N.Y. In general, a fluid coating composition contains a binder, a solvent to dissolve or suspend the components, and optional additives such as surfactants, dispersants, plasticizers, biocides, cross-linking agents for toughness and insolubility, and conductive materials to minimize static buildup. All the components are mixed and dissolved or dispersed, and the coating fluid is sent to an applicator where it is applied to a substrate by one of several coating techniques. Heat is then applied to the coating to evaporate the solvent and produce the desired film, or the coating is solidified by the action of ultraviolet radiation or an electron beam.

The most suitable coating method—including the coating speed—will depend on the quality and functionality desired and the materials being used, e.g., the substrate, the solvent, weight and viscosity of the coating, etc. For a single layer format, suitable coating methods may include dip coating, rod coating, knife coating, blade coating, air knife coating, gravure coating, forward and reverse roll coating, and slot and extrusion coating.

Coating speed can also be an important determinant in the choice of coating method. Although most methods can be used at low speeds, and all methods have a limiting upper speed, some work better at higher speeds. Curtain coating requires a minimum flow to maintain the integrity of the curtain. Therefore, this method is limited to higher speeds if a thin coating is to be obtained. In slide coating of multiple layers, interfacial instabilities are more likely to occur on the slide when the layers are very thin. Higher speeds, with their higher flows and thicker layers on the slide, tend to avoid these instabilities. See, p. 12, "Modern Coating and Drying Technology", supra.

The gelatin has a laydown of 0.2 to 100 grams per square meter; preferably 10 to 50 grams per square meter.

Any well known coating method, such as bead coating or curtain coating, can be used to prepare the gelatin substrate. The gelatin could be coated with any other coating aids such as surfactants and thickeners to adjust its physical property. The gelatin used in the invention may be chemically modified either before, during or after the coating process to create more chemical functionalities that can react or interact with biologically active molecules or assemblies intended to be attached on this substrate.

In general, there are two ways to prepare a reactive surface for protein capture agent immobilization using gelatin coating method. In the first approach, the chemical agent or polymer scaffold can be mixed with gelatin with certain coating aids and the mixture is coated on a solid support as described. In the second approach, a gelatin coating is prepared on a solid support as described above, and upon drying, the gelatin coating is dipped into a solution containing chemical agents, e.g. A-L-B, polymer scaffold, to affix the reactive chemistry to the gelatin surface. It is preferred that the polymer scaffold is introduced to the substrate surface during gelatin coating to simplify the manufacture process.

Once a protein microarray substrate is modified with the polymer scaffold, protein capture agents will be placed onto the substrate to generate protein microarray content. Protein capture agents are molecules that can interact with proteins in high affinity and high specificity. Typically it is desirable to have an affinity binding constant between a protein capture agent and target protein greater than 106 M-1. There are several classes of molecules that can be used as protein capture agents on a protein microarray. Antibodies are a class of naturally occurring protein molecules that are capable of binding targets with high affinity and specificity. The properties and protocols of using antibody can be found in *"Using Antibodies; A Laboratory Manual"*, (Cold Spring Harbor Laboratory Press, by Ed Harlow and David Lane, Cold Spring Harbor, N.Y. 1999). Antigens can also be used as protein capture agents if antibodies are intended targets for detection. Protein scaffolds such as whole protein/ enzyme or their fragments can be used as protein capture agents as well. Examples include phosphotases, kinases, proteases, oxidases, hydrolyases, cytokines, or synthetic peptides. Nucleic acid ligands can be used as protein capture agent molecules after in vitro selection and enrichment for their binding affinity and specificity to certain targets. The principle of such selection process can be found in *Science*, Vol. 249, 505–510, 1990 and *Nature*, Vol. 346, 818–822, 1990. U.S. Pat. No. 5,110,833 discloses an alternative class of synthetic molecules that can mimic antibody binding affinity and specificity and can be readily prepared by the so called Molecular Imprinting Polymer (MIP). This technology has been reviewed in *Chem. Rev.* Vol. 100, 2495–2504, (2000).

In practice, a protein microarray is brought into contact with a biological fluid sample, proteins in the sample will adsorb to both areas spotted with specific protein capture agents and areas without protein capture agents. Since the protein microarray is intended to be used for the measurement of specific interactions between protein capture agents on the chip with certain proteins or other molecules in the biological fluid sample, the non-specific binding of sample proteins to non-spotted area would give rise to high background noise. The term non-specific binding refers to the tendency of protein molecules to adhere to a solid surface in a non-selective manner. This high background noise resulting from the non-specific binding will interfere with reporter signals to be detected from the spotted area unless the non-specific binding is blocked in an appropriate manner. Typically, the protein microarray will be immersed in a solution containing a blocking agent to block the non-specific binding sites before its contact with the intended analyte solution. A commonly used method for blocking protein non-specific binding is to treat the surface of the substrate with a large excess of bovine serum albumin. The non-spotted surface area may also be chemically modified with polyethylene glycol (PEG), phospholipid, or poly lysine to prevent non-specific binding.

The invention can be better appreciated by reference to the following specific embodiments.

EXAMPLES

Example 1

This example illustrates the formulation of gelatin melt and the method of coating the melt onto a reflective support.

Formulation 1-1
This was prepared by adding 3.0 grams of Type IV gelatin in 9.1 grams of water, 0.032 grams of coating aid of Nonylphenoxypolyglycerol in 0.3 grams of water, 0.06 grams of coating aid Sodium octyl phenol poly (etheneoxy) sulfonate in 0.8 grams of water, 0.15 grams of Ethene, 1,1'-(methylenebis(sulfonyl))bis-in 8.25 grams water and 98.3 grams of distilled water.

Formulation 1-2
This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.30 grams of Ethene, 1,1'-(methylenebis(sulfonyl))bis-in 16.5 grams water and 89.9 grams of distilled water.

Formulation 1-3
This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.45 grams of Ethene, 1,1'-(methylenebis(sulfonyl))bis-in 24.75 grams water and 81.5 grams of distilled water.

Formulation 1-4
This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.60 grams of Ethene, 1,1'-(methylenebis(sulfonyl))bis-in 32.9 grams water and 73.2 grams of distilled water.

Formulation 1-5
This was prepared by adding 3.0 grams of Type IV gelatin in 9.1 grams of water, 0.032 grams of coating aid Nonylphenoxypolyglycerol in 0.3 grams water, 0.06 grams of coating aid Sodium octyl phenol poly (etheneoxy) sulfonate in 0.8 grams water, 0.75 grams of Ethene, 1,1'-(methylenebis(sulfonyl))bis-in 41.15 grams of water and 64.8 grams of distilled water.

Formulations 1-1 to 1-5 were coated on a reflective photographic paper substrate using the coating device shown in Formula II. The formulations were introduced through a slot coating die at a temperature of 45° C. onto a 12.7 cm wide web moving at the rate of 3.7 m/min. The flow rate was adjusted to provide a level of 86.1 g/m² gelatin coverage. The coatings were chill-set in a 2.4 m long chilling section that was maintained at a temperature of 4° C. and 56.6% RH and then dried in two drying sections that were 9.8 m and 11.6 m in length respectively. The first drying section was maintained at a temperature of 21° C. and 33.2% RH and the second was maintained at a temperature of 37.8° C. and 18.6% RH.

Example 2

This example illustrates the method of evaluating gelatin coating using a modified enzyme linked immunosobent assay (ELISA).

The procedure to perform the modified ELISA is follows.

1. Goat anti-mouse antibody IgG from Sigma was dissolved in PBS (phosphate saline buffer, pH7.4) buffer to a concentration of 1 mg/mL. A series of diluted of goat anti-mouse antibody IgG were spotted manually onto nitrocellulose membrane and coated gelatin substrates. The spotted substrates were incubated in a humid chamber for 1 hour at room temperature.

2. The substrates were washed four times in PBS buffer with 1% Triton X100™, 5 min each time with shaking.

3. The washed substrates were incubated in PBS buffer with 1% glycine for 15 min with constant shaking.

4. The substrates were washed four times in PBS buffer with 1% Triton™ X100 with shaking.

5. Mouse IgG from Sigma was diluted in PBS buffer with 0.1% Tween™ 20 to 1 μg/mL to cover the whole surface of substrates, and the substrates were incubate at room temperature for 1 hour.

6. The substrates were washed four times with PBS buffer with 1% Triton X100, 5 min each time with constant shaking.

7. The substrates were incubated in goat anti-mouse IgG horse raddish peroxidase conjugate (diluted in PBS with 1% glycine to appropriate titer) solution to cover the whole surface of the substrates at room temperature for 1 hour with shaking.

8. The substrates were washed four times with PBS buffer with 1% Triton X100, 5 min each time with constant shaking, and rinsed twice in water.

9. The color was developed in horse raddish peroxidase substrate solution containing 3,3'-diaminobenzidine tetrahydrochloride (DAB) from Sigma following manufacture's recommendation.

The substrates with color developed on their surfaces were air-dried and the reflection densities of the spotted area and non-spotted area were measured on a Perkin-Elmer PDS microdensitometer with Status 'A' filtration. The data are shown in Table 1.

TABLE 1

| Sample ID | BVSM level vs total gelatin | Spot density with 100 ng of goat anti-mouse IgG | Spot density with 75 ng of goat anti-mouse IgG | Spot density with 50 ng of goat anti-mouse IgG | Spot density with 0 ng of goat anti-mouse IgG, background density | Comments |
|---|---|---|---|---|---|---|
| Nitrocellulose membrane | N/A | 0.86 | 0.74 | 0.60 | 0.41 | Comparative |
| 1-1 | 2% | 0.36 | 0.17 | 0.13 | 0.10 | Invention |
| 1-2 | 4% | 0.50 | 0.27 | 0.20 | 0.11 | Invention |
| 1-3 | 6% | 0.52 | 0.35 | 0.26 | 0.12 | Invention |
| 1-4 | 8% | 0.55 | 0.38 | 0.28 | 0.12 | Invention |
| 1-5 | 10% | 0.56 | 0.40 | 0.30 | 0.12 | Invention |

All five inventive examples gave much lower background densities that were caused by non-specific protein binding to the surface compared to the nitrocellulose membrane control sample.

Example 3

This example illustrates the modification of coated gelatin surface using a polymeric primary amine to further improve its protein immobilization capacity.

Synthesis of poly (N-(3-aminopropyl) methacrylamide hydrochloride):25.00 g of N-(3-aminopropyl) methacrylamide hydrochloride and 1.25 g of 2,2'-azobis(2-methylpropionamidine) dihydrochloride were dissolved in 125 g of 4:1 water:isopropanol in a 500 ml round bottomed flask fitted with a rubber septum secured with a nylon strap tie. The polymerization solution was bubble degassed with nitrogen for 10 minutes and heated for 4 hours in a water bath at 70° C. The resulting clear, viscous solution was dialyzed overnight using dialysis tubing with 1000 MW cutoff and concentrated via rotary evaporation to afford 150 ml of a solution of 13.5% solids. The PEO-relative molecular weights (determined by SEC in water) were determined to be: Mn=11,900; Mw=25,800.

3-1: Gelatin was coated according to Example 1 and the coating was immersed in 0.01 M acetate buffer pH5.0 containing 10 mM of 2-(4-Dimethylcarbomoyl-pyridino)-ethane-1-sulfonate and two percent of poly (N-(3-aminopropyl) methacrylamide hydrochloride). The mixture was agitated at room temperature for one hour and rinsed three times with distilled water. Then, and the coating was immersed in 0.01 M phosphate buffer pH7.0 containing 10 mM N-(γ-maleimidobutyryloxy) succinimide ester. The reaction was allowed to proceed for 1 hours at room temperature and the coating was rinsed with distilled water and air-dried.

3-2: Gelatin was coated according to Example 1 and the coating was immersed in 0.01 M acetate buffer pH5.0 containing 10 mM of 2-(4-Dimethylcarbomoyl-pyridino)-ethane-1-sulfonate and two percent of polyethyleneimine (MW 2000, purchased from Aldrich as 50% solution). The mixture was agitated at room temperature for one hour and rinsed three times with distilled water. Then, and the coating was immersed in 0.01 M phosphate buffer pH7.0 containing 10 mM N-(γ-maleimidobutyryloxy) succinimide ester. The reaction was allowed to proceed for 1 hour at room temperature and the coating was rinsed with distilled water and air-dried.

3-3: Gelatin was coated according to Example 1 and the coating was immersed in 0.01 M phosphate buffer pH7.0 containing 10 mM NHS-PEG-Maleimide (MW3400, purchased from Shearwater Co.). The mixture was agitated at room temperature for one hour and rinsed with distilled water and air-dried.

Goat anti-mouse antibody for spotting was reduced in 0.05 M DTT and allowed to stand at room temp for 10 min. Immediately prior to use, the reduced antibody solution was extracted four times with ethyl acetate to remove DTT from sample. The DTT treated goat anti-mouse antibody was spotted onto substrate surface and evaluated essentially as described in Example 2 except that cysteine was used instead of glycine in step 2 and 7.

The evaluation results for protein surface binding capacity are shown in Table 2

TABLE 2

| Sample ID | Spot density with 10 ng of goat anti-mouse IgG | Spot density with 5 ng of goat anti-mouse IgG | Spot density with 1 ng of goat anti-mouse IgG | Spot density with 0 ng of goat anti-mouse IgG, background density | Comments |
|---|---|---|---|---|---|
| 1-1 | N/A* | N/A* | N/A* | 0.08 | Comparative |
| 3-1 | 0.40 | 0.25 | 0.12 | 0.08 | Invention |
| 3-2 | 0.36 | 0.20 | 0.06 | 0.07 | Invention |
| 3-3 | 0.22 | N/A* | N/A* | 0.09 | Comparative |

*No spot signal can be detected at these levels of goat anti-mouse IgG. Treatment of gelatin surfaces with polymeric amines improved protein surface binding capacity and allowed lower laydown (signals were readily detectable with 1 nano grams of protein spotted on the modified surfaces) of detection antibody molecules.

Example 4

This example illustrates the modification of coated gelatin surface using polymers containing vinylsulfone-functionalities to further improve protein immobilizaton capacity.

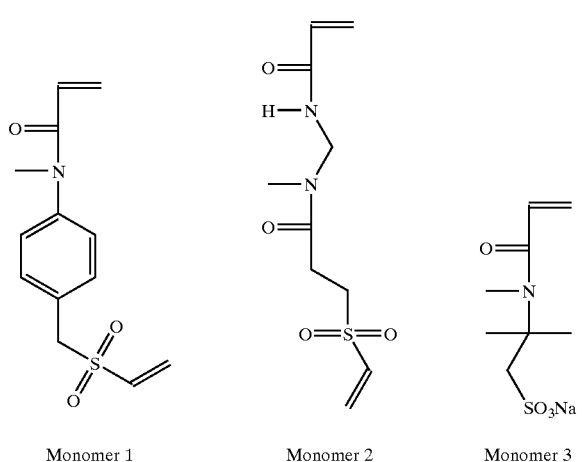

Formula II

Monomer 1  Monomer 2  Monomer 3

Synthesis of Polymer 1

45.5:54.5 Copolymer of Monomer 1 and Monomer 3

1] Synthesis of chloroethanesulfone-containing Precursor Polymer: N-[4-[[(2-chloroethyl)sulfone]methyl]phenyl] acrylamide (22.5 g), sodium 2-acrylamido-2-methanepropionate (34.5 g of a 52.2% w/w solution in water), and 4,4'-azobis(cyanovaleric acid) (0.76 g) were dissolved in 160.0 g N-methyl pyrrolidinone in a 1 L 3-neck round bottom flask outfitted with a mechanical stirrer, condenser, and nitrogen inlet. The solution was bubble degassed with nitrogen for 10 minutes and heated for 16 hours at 65° C. The resulting solution was precipitated into 3 L propyl acetate to produce a fine powder which was recovered by filtration. The crude product was redissolved in 300 ml methanol and precipitated again into 3 L isopropyl ether. The resulting powder was collected by filtration and dried in a vacuum oven at 80° C. for 48 hours to afford 38.6 g of a white powder. The chloroethylsulfone content of the polymer was determined to be 1.776 mEq/g by titration with NaOH which is equivalent to a polymer 45.5 mol % monomer 1. Size exclusion chromatography (SEC) of the polymer in hexafluoroisopropanol gave absolute molecular weights of Mn=12,800 and Mw=36,500.

2] Elimination Reaction: 20.0 g of the product chloroethysulfone-containing polymer was dissolved in 144.5 mL deionized water. 35.5 mL of 1N NaOH was added and the solution was stirred at room temperature for 1 hour, at which point the pH had dropped to ~7. The polymer was stored as an aqueous solution of 9.81% solids.

Synthesis of Polymer 2

44.3:55.7 Copolymer of Monomer 1 and Monomer 3

1] Synthesis of chloroethanesulfone-containing Precursor Polymer: N-[4-[[(2-chloroethyl)sulfone]methyl]phenyl] acrylamide (22.5 g), sodium 2-acrylamido-2-methanepropionate (34.5 g of a 52.2% w/w solution in water), and 4,4'-azobis(cyanovaleric acid) (0.76 g) were dissolved in 95.0 g N-methyl pyrrolidinone in a 500 mL 3-neck round bottom flask outfitted with a mechanical stirrer, condenser, and nitrogen inlet. The solution was bubble degassed with nitrogen for 10 minutes and heated for 16 hours at 65° C. The resulting solution was precipitated into 3 L propyl acetate to produce a white, sticky semisolid from which the solvents were decanted. The crude product was redissolved in 300 ml methanol and precipitated again into 3 L isopropyl ether. The resulting tacky solid was isolated by decanting the solvents and was dried in a vacuum oven at 80° C. for 48 hours to afford 42.5 g of a white powder. The chloroethylsulfone content of the polymer was determined to me 1.732 mEq/g by titration with NaOH which is equivalent to a polymer 44.3 mol % monomer 1. Size exclusion chromatography (SEC) of the polymer in hexafluoroisopropanol gave absolute molecular weights of Mn=33,800 and Mw=96,300.

2] Elimination Reaction: 20.0 g of the product chloroethysulfone-containing polymer was dissolved in 145.4 mL deionized water. 34.6 mL of 1N NaOH was added and the solution was stirred at room temperature for 1 hour, at which point the pH had dropped to ~7. The polymer was stored as an aqueous solution of 9.94% solids.

Synthesis of Polymer 3

33.4:66.6 Copolymer of Monomer 2 and Monomer 3

1] Synthesis of chloroethanesulfone-containing Precursor Polymer: N-[3-(2-chloroethylsulfone) propanamidomethyl] acrylamide (18.0 g) was dissolved in 210 mL N-methyl pyrrolidinone, filtered to remove a small amount of insoluble gels, and bubble degassed for 10 minutes with nitrogen. A second solution of sodium 2-acrylamido-2-methanepropionate (40.7 g of a 52.2% w/w solution in water), isopropanol (50 mL), deionized water (50 mL), dodecanethiol (0.4 mL) and 4,4'-azobis (cyanovaleric acid) (0.72 g) was prepared and similarly degassed. The two solutions were combined in a 1 L round bottom and sealed with a rubber septum fastened with a plastic strap tie. After heating for 16 hours at 65° C., the low boiling solvents were stripped using a rotary evaporator and the remaining solution was precipitated into 3L isopropyl ether to afford a thick semisolid from which the solvents were decanted. The product was redissolved in 250 ml 250 mL methanol and again precipitated into 3L isopropyl ether. A fine powder was recovered by filtration and dried in a vacuum oven at 70° C. for 48 hours to afford 34.56 g of a white powder. The chloroethylsulfone content of the polymer was determined to me 1.35 mEq/g by titration with NaOH which is equivalent to a polymer 33.39 mol % monomer 1. Size exclusion chromatography (SEC) of the polymer hexafluoroisopropanol gave absolute molecular weights of Mn=10,900 and Mw=26,000.

2] Elimination Reaction: 15.00 g of the product chloroethysulfone-containing polymer was dissolved in 114.75 mL deionized water. 20.25 mL of 1N NaOH was added and the solution was stirred at room temperature for 1 hour, at which point the pH had dropped to ~7. The polymer was stored as an aqueous solution of 10.25% solids.

Synthesis of Polymer 4

47.4:52.6 copolymer of Monomer 1 and Monomer 3

1] Synthesis of chloroethanesulfone-containing Precursor Polymer: N-[4-[[(2-chloroethyl)sulfone]methyl]phenyl] acrylamide (27.00 g), sodium 2-acrylamido-2-methanepropionate (26.00 g of a 52.2% w/w solution in water), and 4,4'-azobis(cyanovaleric acid) (0.76 g) were dissolved in 260 g N-methyl pyrrolidinone in a 1L mL 3-neck round bottom flask outfitted with a mechanical stirrer, condenser, and nitrogen inlet. The solution was bubble degassed with nitrogen for 10 minutes and heated for 4 hours at 65° C. The resulting solution was precipitated into 3 L 1:1 acetone:ethyl acetate to produce a hygroscopic, fine white powder which was isolated by filtration. The crude product was redissolved in 200 ml methanol and precipitated again into 3 L isopropyl ether. The resulting coarse precipitate was isolated by filtration and was dried in a vacuum oven at 70° C. for 24 hours to afford 26.59 g of a white powder. The chloroethylsulfone content of the polymer was determined to 1.840 mEq/g by titration with NaOH which is equivalent to a polymer 47.4 mol % monomer 1. Size exclusion chromatography (SEC) of the polymer in hexafluoroisopropanol gave absolute molecular weights of Mn=5,720 and Mw=17,700.

2] Elimination Reaction: 15.00 g of the product chloroethysulfone-containing polymer was dissolved in 107.40 mL deionized water. 27.60 mL of 1N NaOH was added and the solution was stirred at room temperature for 1 hour, at which point the pH had dropped to ~7. The polymer was stored as an aqueous solution of 10.42% solids.

4-1: Gelatin was coated according to Example 1 and the coating was immersed in 0.01 M phosphate buffer pH7.0 containing 1% of polymer 1. The mixture was agitated at room temperature for three hour and rinsed with distilled water and air-dried.

4-2: Gelatin was coated according to Example 1 and the coating was immersed in 0.01 M phosphate buffer pH7.0 containing 1% of polymer 2. The mixture was agitated at room temperature for three hour and rinsed with distilled water and air-dried.

4-3: Gelatin was coated according to Example 1 and the coating was immersed in 0.01 M phosphate buffer pH7.0 containing 1% of polymer 3. The mixture was agitated at room temperature for three hour and rinsed with distilled water and air-dried.

4-4: Gelatin was coated according to Example 1 and the coating was immersed in 0.01 M phosphate buffer pH7.0 containing 1% of polymer 4. The mixture was agitated at room temperature for three hour and rinsed with distilled water and air-dried.

The evaluation was performed using ELISA assay as described in Example 2 except the final signal was detected as chemiluminescence instead of color development as described in step 9 of ELISA protocol. The chemiluminescence image was capture by contacting a thin layer of SuperSignal® ELISA chemiluminescence substrate solution (purchased from PIERCE ENDOGEN) with coated substrate. The emission was measured on Kodak Image Station 440 and quantified using Region of Interest (ROI) software supplied with the instrument. The evaluation results for protein surface binding capacity are shown in Table 3.

TABLE 3

| Sample ID | Spot density with 10 ng of goat anti-mouse IgG | Spot density with 5 ng of goat anti-mouse IgG | Spot density with 1 ng of goat anti-mouse IgG | Comments |
| --- | --- | --- | --- | --- |
| 1-1 | 865 | 150 | 146 | Comparative |
| 1-4 | 1437 | 483 | 447 | Comparative |

TABLE 3-continued

| Sample ID | Spot density with 10 ng of goat anti-mouse IgG | Spot density with 5 ng of goat anti-mouse IgG | Spot density with 1 ng of goat anti-mouse IgG | Comments |
| --- | --- | --- | --- | --- |
| 4-1 | 2216 | 1907 | 901 | Invention |
| 4-2 | 1859 | 1754 | 1002 | Invention |
| 4-3 | 3321 | 2017 | 1225 | Invention |
| 4-4 | 3831 | 2019 | 1389 | Invention |

*No spot signal can be detected at these levels of goat anti-mouse IgG.
Note,
for example, four polymeric vinylsulfone modified gelatin surface show significant improvement in protein binding capacity over the comparative examples.

Example 5

This example illustrates the non-specific binding to protein of coated gelatin surface.

A silicon wafer or glass was treated with 10% wt. NaOH solution in ethanol for 10 min and annealed at 580° C. for 30 min. A 1 wt. % 3-aminopropyltriethoxylsilane (APS, form Gelest Inc.) aqueous solution was prepared and adjusted to pH 3.5 by using acetic acid. After placing the treated wafer or glass in the APS solution, pH of the solution was adjusted to 5.5 with NaOH. The reaction was allowed for 1 hour, then the surface rinsed thoroughly with water, and dried in nitrogen. The APS layer affixed on glass or wafer surface was measured with ellipsometry (GAERTNER® L116B) and found to have a thickness of 8 Å. The gelatin and polyethylenimine (PEI) surfaces were further derived by first treating the APS surface with a 10 mM cyanic chloride (from Aldrich®) in acetonitrile solution for one hour, and then dipping the slides in 0.1% wt solutions of gelatin and PEI (from Aldrich®, MW ~2000) for over night. The surfaces were found to have bonded a layer of gelatin and PEI with the thickness of 47 Å and 30 Å, respectively.

The protein non-specific bonding to the three amine functional group containing surfaces was tested by soaking the APS, gelatin and PEI coated slides in a 100 µg/ml bovine serum albumin (BSA, from Sigma®) solution in pH=7 phosphate buffer solution for 60 min and rinse with water for 2 min. The amounts of BSA non-specifically adsorbed to the surfaces were determined by ellipsometry. The results are shown in Table 4:

TABLE 4

BSA Non-Specific Bonding to Amine Containing Surfaces of Gelatin, APS, and PHI

| Gelatin | APS | PEI |
| --- | --- | --- |
| 6Å | 10Å | 13Å |

The results show that the gelatin surface has significantly lower non-specific bonding capacity than the other amine functional group containing materials. Note, for example, that the gelatin coated surface absorbs significantly less BSA than the amine coated surfaces.

The invention has been described in detail with particular reference to certain preferred embodiments thereof, but it will be understood that variations and modifications can be effected within the spirit and scope of the invention.

What is claimed is:

1. A gelatin-based substrate for fabricating protein arrays, the substrate comprising:

gelatin having at least one surface;
a polymer scaffold affixed to the gelatin surface; and
a trifunctional compound A-L-B;
wherein A is a functional group capable of interacting with the polymer scaffold; L is a linking group capable of interacting with A and with B; and B is a specific functionality that provides one or more reactive units capable of interacting with a protein capture agent.

2. The gelatin-based substrate of claim 1 wherein the reactive unit is aldehyde, epoxy, hydrazide, vinyl sulfone, succinimidyl ester, carbodiimide, maleimide, dithio, iodoacetyl, isocyanate, isothiocyanate, or aziridine.

3. The gelatin-based substrate of claim 1 wherein the polymer scaffold comprises a precursor polymer including thiols, amines, phosphines, alcohols, or carboxylic acids.

4. The gelatin-based substrate of claim 3 wherein the precursor polymer is rich in primary or secondary amines.

5. The gelatin-based substrate of claim 1 wherein A may be the same or different from B.

6. The gelatin-based substrate of claim 1 wherein the interaction between the gelatin and the polymer scaffold is a covalent bond.

7. The gelatin-based substrate of claim 1 wherein the interaction between the scaffold and A is a physical binding or a chemical reaction.

8. The gelatin-based substrate of claim 1 wherein the interaction between the protein capture agent and B is a physical binding or a chemical reaction.

9. The gelatin-based substrate of claim 1 wherein the polymer forming the polymer scaffold is represented by Formula I:

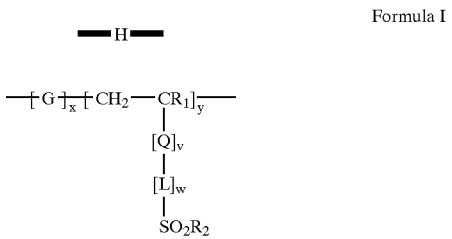

Formula I wherein $R_1$ is a hydrogen atom or a $C_1$–$C_6$ alkyl group; Q is —$CO_2$—, or $CONR_1$; v is 1 or 0; w is 1–3; L is a divalent linking group containing at least one linkage selected from the group consisting of —$CO_2$— and —$CONR_1$, and containing 3–15 carbon atoms, or a divalent unit containing at least one linkage selected from the group consisting of —O—, —$N(R_1)$—, —CO—, —SO—, —$SO_2$—, —$SO_3$—, —$SO_2N(R_1)$—, —$N(R_1)CON(R_1)$— and —$N(R_1)CO_2$—, and containing 1–12 carbon atoms in which $R_1$ has the same meaning as defined above; $R_2$ is —CH=$CH_2$ or —$CH_2$—$CH_2X_1$ wherein $X_1$ is a substituent replaceable by a nucleophilic group or releasable in the form of $HX_1$ by a base; $X_1$ is —$S_2O_3^-$, —$SO_4^-$, —Cl, —Br, —I, quaternary ammonium, pyridinium, or —CN, and sulfonate esters; x and y both represent molar percentages ranging from 10 to 90 and 90 to 10; G comprises repeating units of an α, β-ethylenically unsaturated addition polymerizeable monomer that imparts water-solubility to the polymer; and monomer H is the polymerized form of a vinylsulfone or vinylsulfone precursor unit covalently bound to a polymerizeable α, β-ethylenically unsaturated function by an organic spacer which consists of Q and L, of which Q is an optional component.

10. The gelatin-based substrate of claim 9 wherein H in the formula I contains a vinylsulfone moiety or a vinylsulfone precursor.

11. The gelatin-based substrate of claim 10 wherein H in the formula I comprises a dehydrochiorinated form of a chioroethylsulfone-containing unit.

12. The gelatin-based substrate of claim 9 wherein G in the formula I comprises repeating units of acrylamide, sodium 2-acrylamido-2-methanepropionate, sulfopropyl acrylate and methacrylate salts, or sodium styrenesulfonate.

13. The gelatin-based substrate of claim 1 wherein the polymer forming the polymer scaffold is poly(vinylamine), poly(propyleneimine), poly(N-aminopropyl methacrylamide) or poly(n-vinylimidazole).

14. The gelatin-based substrate of claim 1 wherein either A or B, or both, is aldehyde, epoxy, hydrazide, vinyl sulfone, succinimidyl ester, carbodiimide, maleimide, dithio, iodoacetyl, isocyanate, isothiocyanate, or aziridine.

15. The gelatin-based substrate of claim 1 wherein B is an affinity tag capable of interacting non-covalently with a protein capture agent.

16. The gelatin-based substrate of claim 1 wherein B is streptavidin, biotin, glutathione-S-transferase, glutathione, or histidine tags.

17. The gelatin-based substrate of claim 1 wherein L is a diradical of such a length that the shortest through-bond path between the ends that connect A to B is not greater than 10 atoms.

18. The substrate of claim 1 wherein the gelatin is alkaline pretreated.

19. The substrate of claim 1 wherein the gelatin is pig gelatin or fish gelatin.

20. The substrate of claim 1 wherein the gelatin coverage is 0.2 to 100 grams per square meter.

21. The substrate of claim 1 wherein the gelatin coverage is 10 to 50 grams per square meter.

22. The substrate of claim 1 further comprising a protein capture agent in physical or chemical interaction with B.

23. The substrate of claim 1 wherein the protein capture agent is an antibody, a protein scaffold, a peptide, a nucleic acid ligand or a molecular imprinting polymer.

24. A method of making the gelatin-based substrate of claim 1, comprising the steps of:

providing a support;
coating on the support a composition containing gelatin;
affixing a polymer scaffold to a surface of the gelatin; and
bonding a trifunctional compound A-L-B to the polymer scaffold;

wherein A is a functional group capable of bonding to the polymer scaffold; L is a linking group capable of connecting A with B; and B is a reactive unit that provides one or more reactive units capable of interacting with a protein or protein capture agent.

25. The method of claim 24 wherein the trifunctional compound ALB is affixed while coating the gelatin on the substrate.

26. The method of claim 24 wherein the trifunctional compound ALB is affixed after coating the gelatin on the substrate.

27. The method of claim 24 wherein the protein capture agent is antibody, protein scaffold, peptide, nucleic acid ligand, or a molecular imprinting polymer.

* * * * *

UNITED STATES PATENT AND TRADEMARK OFFICE
CERTIFICATE OF CORRECTION

PATENT NO. : 6,815,078 B2
DATED : November 9, 2004
INVENTOR(S) : Tiecheng A. Quio et al.

It is certified that error appears in the above-identified patent and that said Letters Patent is hereby corrected as shown below:

Column 18,
Line 3, please delete "chioroethylsulfone-containing" and in place therof, insert
-- chloroethylsulfone-containing --

Signed and Sealed this

Second Day of August, 2005

JON W. DUDAS
*Director of the United States Patent and Trademark Office*